United States Patent [19]

Wernicke et al.

[11] Patent Number: 5,269,303

[45] Date of Patent: Dec. 14, 1993

[54] TREATMENT OF DEMENTIA BY NERVE STIMULATION

[75] Inventors: Joachim F. Wernicke, League City; Reese S. Terry, Jr., Houston, both of Tex.

[73] Assignee: Cyberonics, Inc., Webster, Tex.

[21] Appl. No.: 660,404

[22] Filed: Feb. 22, 1991

[51] Int. Cl.$^5$ ............................................. A61N 1/36
[52] U.S. Cl. ....................................... 607/45; 607/59; 607/72; 607/118; 607/62
[58] Field of Search ............. 128/784.5, 642, 421–423, 128/419 R, 419 C, 420.5, 731, 732

[56] References Cited

U.S. PATENT DOCUMENTS 4,867,164  9/1989  Zabara ................................ 128/421

OTHER PUBLICATIONS

Ettlin et al., *Arch. Nerol.*, 46; Nov. 1989, pp. 1217–1220.
Verma et al., *Clin. Electroencephalog.*, 1987, vol. 18, No. 1, pp. 26–33.
Hughes et al., *Clin. Electroencephalog.*, 1989, vol. 20, No. 2, pp. 77–85.
Kurlychek, *J. Clin. Psychol.*, Jan. 1989, vol. 45, No. 1, pp. 117–123.
Rettig et al., Changes in Neuropsychological and Personality Functioning in Patients Undergoing Chronic Vagal Nerve Stimulation for control of Partial Siezures, Feb. 5–8, 1992.
T. Erkinjvatti et al., *Acta Neurol. Scand.*, 1988, vol. 77, pp. 36–43.
Rutecki, *Epilipsia, 1990, 31(Suppl. 2): S1–S6.*
Woodbury et al., *Epilepsia,* 1990, 31(Suppl. 2):S7–S19.
Chase, *Exp. Neurol.,* 1966, 16:36–49.

Primary Examiner—Lee S. Cohen
Assistant Examiner—Brian L. Casler

[57] ABSTRACT

A method of treating symptoms of dementia, including cortical dementia, subcortical dementia, and multi-infarct dementia, includes selecting a patient suffering from dementia, and applying to the patient's vagus nerve an electrical stimulation signal having parameter values selected to modulate the electrical activity of the vagus nerve in a manner to modulate the activity of preselected portions of the reticular activating system of the brain stem.

16 Claims, 2 Drawing Sheets

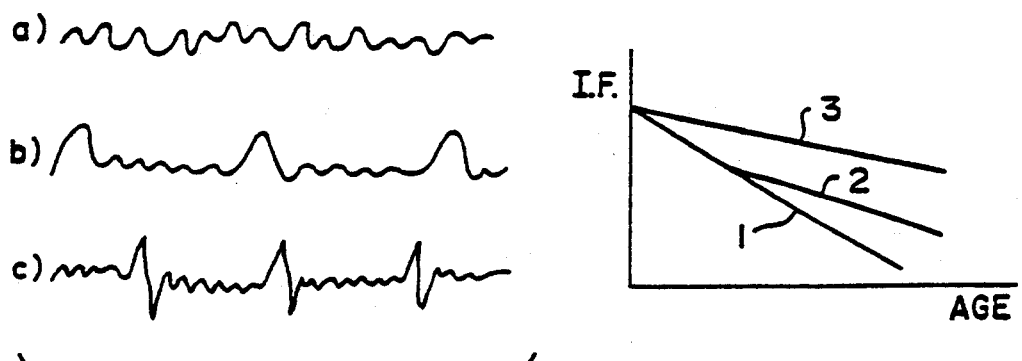
FIG. 1
FIG. 2
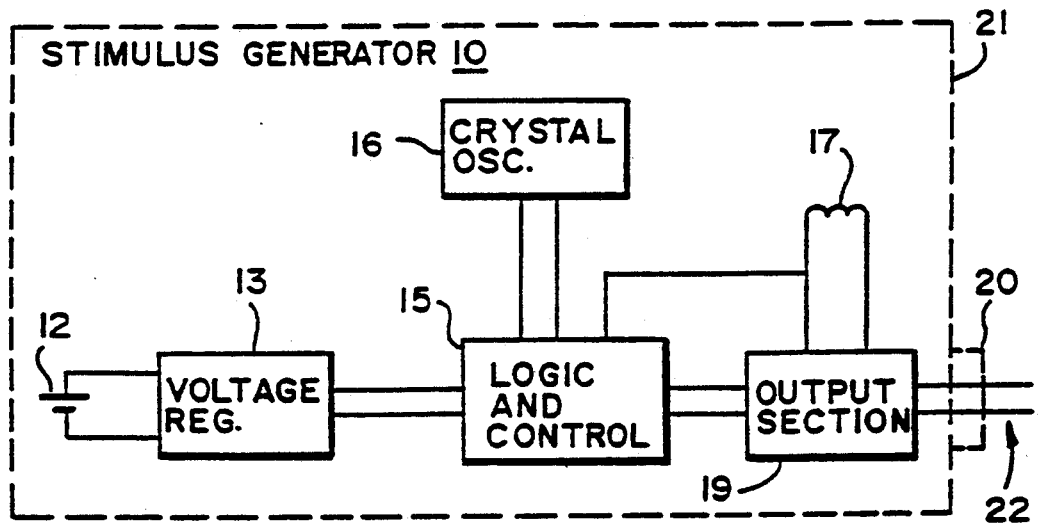
FIG. 3
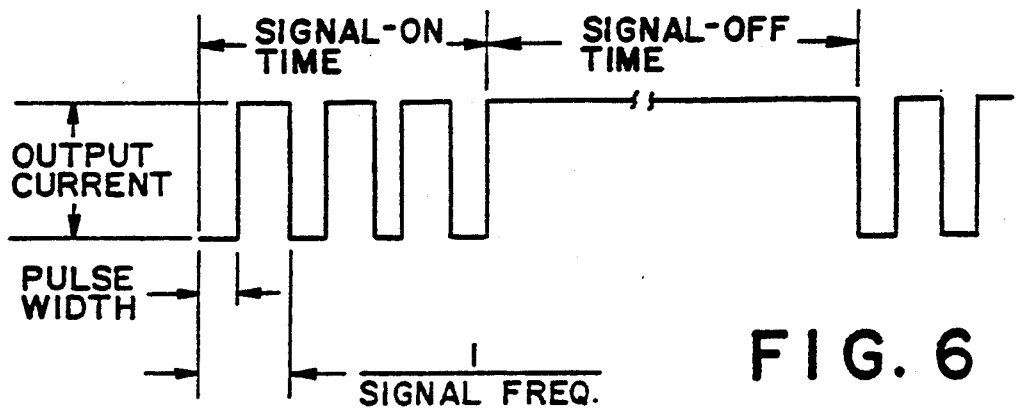
FIG. 6

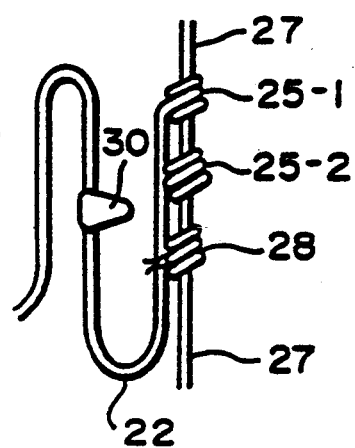
FIG. 5
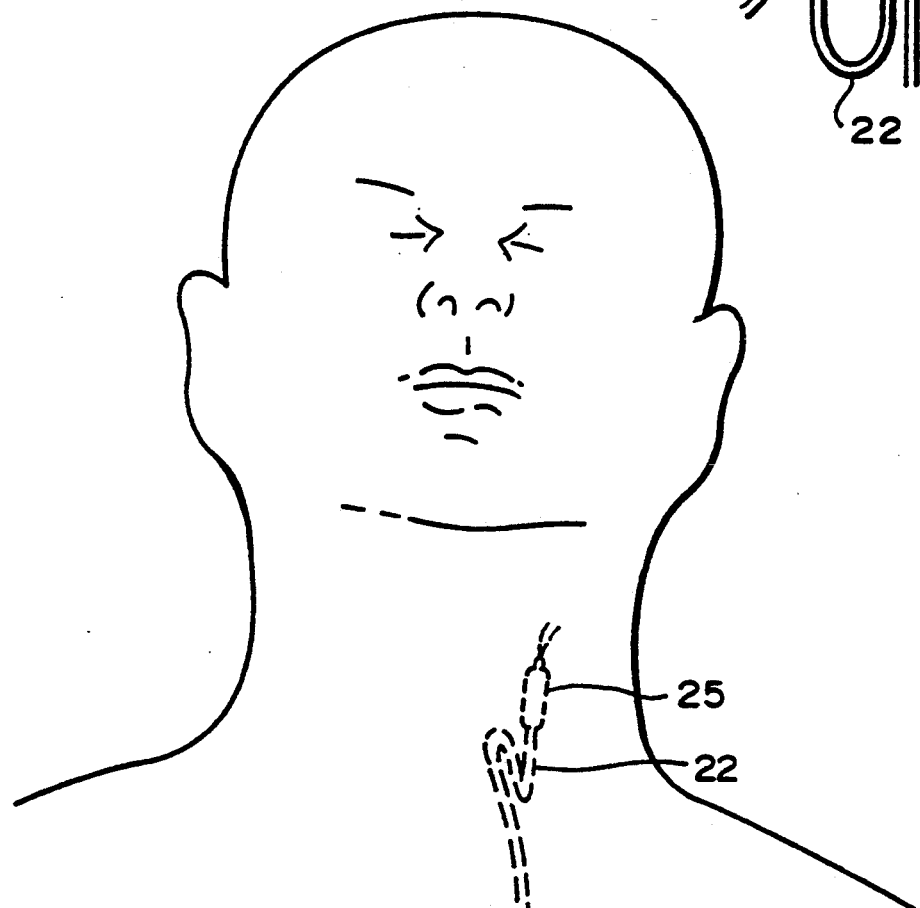
FIG. 4
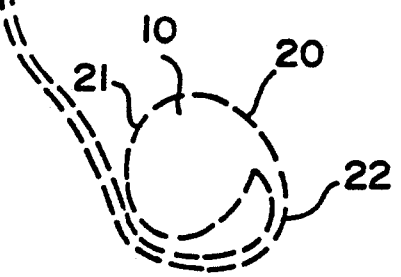

TREATMENT OF DEMENTIA BY NERVE STIMULATION

BACKGROUND OF THE INVENTION

The present invention relates generally to methods and apparatus for treating or controlling medical, psychiatric or neurological disorders by application of modulating electrical signals to a selected nerve or nerve bundle, and more particularly to techniques for treating patients with dementia by application of such signals to the patient's vagus nerve with a neurostimulating device.

Dementia is generally defined as deterioration or loss of intellectual faculties, reasoning power, memory and will due to organic brain disease; characterized by confusion, disorientation, apathy and stupor of varying degrees. It is important to note that although memory and level of alertness may be affected, these are separate processes. Therapies such as stimulants may affect alertness, yet have no effect on intellectual faculties, and therefore are not effective in the treatment of dementia.

Various causes of dementia have been described in the scientific literature, but approximately one-half of all dementia cases are thought to be attributable to Alzheimer's disease. Other common causes of forms of the disorder include numerous small strokes (leading to multi-infarct dementia), and cerebrovascular disease.

The literature also describes the occurrence of electroencephalogram (EEG) changes in patients with dementia. Although results of studies vary somewhat, several findings appear to be fairly consistent. The most common observation seems to be that dementia, especially in patients with Alzheimer's disease, is associated with slowing of the EEG rhythm. Paroxysmal activity is seen less consistently, but in up to half the patients in some series. A review of some relatively recent papers is informative.

Hughes et al. reported in *Clin. Electroencephalog.* (1989) 20(2):77-85, on a study of eighty-three patients with dementia. All were found to have excessive slow wave activity, and the degree of diffuse slowing was correlated with the degree of dementia. Sharp waves, emanating primarily from the temporal lobes, were found to be present in 23 percent of the patients.

In *J. Clin. Psychol.* (1989) 45(1):117-123, Kurlychek observed that in patients with senile dementia of the Alzheimer's type (SDAT), the normal alpha rhythm is usually reduced, and diffuse slower theta and delta waves are more prominent. In multi-infarct dementia, the background alpha rhythm tends to be more preserved, and slowing tends to be more focal rather than diffuse as with SDAT. The EEG tends to be in the normal range in other forms of dementia, such as normal pressure hydrocephalus and Pick's disease.

Ettlin et al., in *Arch. Neurol.* (1989) 46:1217-1220, reported that diagnostic EEG criteria for dementia included overall disturbance (slowing of the dominant rhythm, with appearance of diffuse theta and delta waves), asymmetric findings (localized slow wave activity, paroxysmal activity), and bifrontal burst of delta waves.

Verma et al., in *Clin. Electroencephalog.* (1987) 18(1):26-33, reported finding that 14 out of 15 patients with cortical dementia (such as Alzheimer's and Pick's) had abnormal EEGs. In contrast, the EEG of 14 out of 15 patients with subcortical dementia (associated with conditions such as supranuclear palsy, Huntington's chorea, and Parkinson's disease) tended to be normal. The degree of abnormality tended to correlate with the degree of dementia. Abnormalities consisted primarily of slowing of the background rhythm and excess theta and delta wave activity. Paroxysmal activity was not seen in this series.

An *Acta Nerol. Scand.* (1988) 77:36-43 paper by Erkinjunti et al. reported finding that in patients with Alzheimer's disease, the degree of EEG abnormality correlated to the degree of dementia. Such correlation was not observed in patients with multi-infarct and probable vascular dementia. Focal abnormalities were seen in 18 percent of the Alzheimer's patients. Paroxysmal activity was observed in about 45 percent of patients with Alzheimer's disease, and in even greater numbers with the other types of dementia. The occurrence of paroxysmal activity was not related to the degree of dementia.

Thus far, techniques for treating and/or controlling dementia have had little success. In the main, the treatment of choice has been the use of drugs of various types, including stimulants.

The present invention is directed to methods and devices for treating and controlling dementia by selective stimulation of the vagus nerve (the tenth cranial nerve) in a predetermined manner according to the EEG abnormalities associated with the particular case of the dementia. Several mechanisms are potentially involved. If paroxysmal activity is present, vagal stimulation may serve to suppress this activity. Although paroxysmal activity has not been observed in the majority of cases reported in the papers cited above, it may be present in deeper structures in all dementia patients. Another mechanism by which vagal stimulation can be beneficial in treating dementia is its effect on the reticular formation or activating system, the network of neurons involved in controlling the level of alertness. Stimulation of this system may directly affect alertness and cognitive functions by arousal of higher brain centers.

The neural processes involved in memory are complex, but it is known that hippocampal structures are involved in memory processing. It is postulated further that vagal stimulation can affect hippocampal activity in a way to prevent or inhibit deterioration of memory.

With reference to FIG. 1, simplified representations of the EEGs of persons exhibiting normal activity, excessive slow wave activity, and paroxysmal activity are shown in parts (a), (b) and (c), respectively. In essence, an EEG is a picture of the integration of activity from millions of brain cells, and, in an awake, alert individual, should have the appearance of a noise pattern because the cells are operating independently. Rhythmic alpha activity emanating from the occipital region is normal in such subjects. However, when the brain is driven by a synchronizing force, it may slow the EEG down and produce higher voltage, or cause high voltage synchronous spikes, or spikes and slow waves. In general, the normal person's EEG displays low voltage and relatively fast activity (FIG. 1(*a*)). Situations do occur in which the EEG activity slows down, such as during sleep, and displays higher voltage, but this is normal. In contrast, individuals with dementia, brain tumors and certain other disorders exhibit slow wave activity and higher voltage in an abnormal EEG (FIG. 1(*b*)). Paroxysmal activity is somewhat similar to the latter, but with somewhat faster wave activity and higher synchronous spikes (FIG. 1(*c*)). Both of the EEGs of FIGS. 1(*b*) and (c) are more synchronized than the normal EEG of FIG. 1(a), although that synchrony exists in different ways, e.g., the paroxysmal EEG is more synchronized with faster activity and larger signals.

In studying the intellectual function (I.F.) of individuals versus age, it is observed that the intellectual function of a person with Alzheimer's disease declines much more rapidly than does the intellectual function of the general population with advancing years. A simple plot of I.F. versus age is shown in FIG. 2. Age alone is not indicative of the disease. Advanced age is not invariably associated with loss of function, and it may be argued that all loss of function is related to some abnormal process. An important object of the present invention is to provide a therapy utilizing vagal stimulation which may be instituted at some point on the declining curve 1, representative of a person suffering from Alzheimer's disease or other form of progressive dementia, so as to at least slow down the process and even possibly to arrest the decline. This is indicated by curve 2 which is parallel to or declining at only a moderately faster rate than the normal decline of curve 3 found in the general population. It is unlikely, however, that the patient would experience any reversal of the process. From an efficacy standpoint, the patient population to be treated or likely to experience the most favorable results are those individuals at a moderate stage rather than the more advanced stages of the disease.

Certain anatomical changes that occur with Alzheimer's disease are detectable only during autopsy or brain biopsy, making early diagnosis difficult. Recent findings, however, indicate that neurologic and mental status can be used to diagnose the disease in its early stages. It is somewhat more difficult to correctly diagnose the early stages of certain other types of dementia, such as multi-infarct dementia.

It is known that most nerves in the human body are composed of thousands of fibers, of different sizes designated by groups A, B and C, which carry signals to and from the brain. The vagus nerve, for example, may have approximately 100,000 fibers of the three different types, each carrying signals. Each axon (fiber) of that nerve only conducts in one direction, in normal circumstances. The A and B fibers are myelinated (i.e., have a myelin sheath, constituting a substance largely composed of fat), whereas the C fibers are unmyelinated.

Myelinated fibers are typically larger, conduct faster and have very low stimulation thresholds, compared to the unmyelinated type. Very little energy is required to stimulate the myelinated fibers, and they exhibit a particular strength-duration curve or respond to a specific pulse width versus amplitude for stimulation. The A and B fibers can be stimulated with relatively narrow pulse widths, from 50 to 200 microseconds ($\mu$s), for example. The A fiber conducts slightly faster than the B fiber and has a slightly lower threshold. The C fibers are very small, conduct electrical signals very slowly, and have high stimulation thresholds typically requiring a wider pulse width (300–1000 $\mu$s) and a higher amplitude for activation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

Usually, nerve stimulation activates signals in both directions (bidirectionally). It is possible, however, through the use of special electrodes and waveforms, to selectively stimulate a nerve in one direction only (unidirectionally).

In a paper on the effects of vagal stimulation on experimentally induced seizures in rats (Epilepsia 1990, 31 (Supp 2): S7–S19), Woodbury notes that the vagus nerve is composed of somatic and visceral afferents (inward conducting nerve fibers that convey impulses toward a nerve center such as the brain or spinal cord) and efferents (outward conducting nerve fibers that convey impulses to an effector to stimulate same and produce activity). The vast majority of vagal nerve fibers are C fibers, and a majority are visceral afferents having cell bodies lying in masses or ganglia in the neck. The central projections terminate, by and large, in the nucleus of the solitary tract which sends fibers to various regions of the brain (e.g, the hypothalamus, thalamus, and amygdala); others continue to the medial reticular formation of the medulla, the cerebellum, the nucleus cuneatus and other regions.

Woodbury further notes that stimulation of vagal nerve afferent fibers in animals evokes detectable changes of the EEG in all of these regions, and that the nature and extent of these EEG changes depends on the stimulation parameters. Chase, in *Exp Neurol* (1966) 16:36–49, had also observed that vagal activation can affect the EEG activity of certain parts of the brain. The applicants herein postulate that synchronization of the EEG may be produced when high frequency ($>70$ Hz) weak stimuli activate only the myelinated (A and B) nerve fibers, and that desynchronization of the EEG occurs when intensity of the stimulus is increased to a level that activates the unmyelinated (C) nerve fibers. Woodbury also observes that vagal stimulation can produce widespread inhibitory effects on seizures and certain involuntary movements.

Extra-physiologic electrical stimulation of the vagus nerve has previously been proposed for treatment of epilepsy and various forms of involuntary movement disorders. Specifically, in U.S. Pat. No. 4,702,254 issued Oct. 27, 1987 to J. Zabara (referred to herein as "the '254 patent"), a method and implantable device are disclosed for alleviating or preventing epileptic seizures, characterized by abnormal neural discharge patterns of the brain. The '254 patent describes an implantable neurocybernetic prosthesis (NCP) which utilizes neurocybernetic spectral discrimination by tuning the external current of the NCP generator to the electrochemical properties of a specific group of inhibitory nerves that affect the reticular system of the brain. These nerves are embedded within a bundle of other nerves, and are selectively activated directly or indirectly by the tuning of the NCP to augment states of brain neural discharge to control convulsions or seizures. According to the patent, the spectral discrimination analysis dictates that certain electrical parameters of the NCP pulse generator be selected based on the electrochemical properties of the nerves desired to be activated. The patent further indicates that the optimum sites for application of the NCP generator output to produce the desired effects are the cranial nerves in general, and the vagus nerve in particular.

The NCP disclosed in the '254 patent may be activated either manually or automatically, to provide treatment for the duration of the seizure. Manual activation is performed when the patient experiences the aura at onset of the seizure. Alternatively, automatic activation may be triggered upon detection of instantaneous changes in certain state parameters immediately preceding or at onset of a seizure. Additionally, a prophylactic or preventive mode may be employed in which the NCP is activated periodically to reduce the occurrence and/or the intensity of the seizures. The NCP stimulator of the '254 patent is implanted in the patient's chest and is connected to electrodes installed at the selected point of signal application at the nerve site with the more negative electrode situated closer to the brain and the positive electrode further from the brain, along the vagus nerve.

The '254 patent mentions Parkinson's disease in conjunction with the category of involuntary movement disorders which may be treated with vagal stimulation. The present invention in one of its aspects is directed toward the treatment and control of subcortical dementia, which as a matter of interest encompasses conditions such as Parkinson's disease, Huntington's chorea, and supranuclear palsy. It is noteworthy that the latter forms of dementia involve motor functions that are different from the spasticity or involuntary movement disorders mentioned and proposed for treatment by the methods and apparatus of the '254 patent. For example, Parkinson's disease has several manifestations, one of which is tremor—involuntary movement. But another even more prominent manifestation is the tendency of the patient to react and move very slowly (referred to as bradykinesia)—a reduced amount of voluntary movement. In contrast, then, to involuntary movement disorders addressed in the '254 patent, the aspect of the present invention which is directed toward treatment of subcortical dementia deals in part with brain functions that inhibit or decrease voluntary movement and control. That is, a principal aspect of treatment of dementia according to the invention involves control of the cognitive functions—mental processes of comprehension and reasoning,—but a subordinate aspect involves potential control of voluntary movement functions associated with some types of dementia. In part, the latter is driven by brain stem centers that may be affected by the reticular formation which, in turn, is affected by vagal stimulation.

SUMMARY OF THE INVENTION

The present invention pertains to methods and apparatus employing a neurostimulator (preferably but not necessarily implantable) for application of selective therapy to treat dementia, including cortical dementia such as Alzheimer's disease and Pick's disease; subcortical dementia associated with conditions such as supranuclear palsy, Huntingdon's chorea and Parkinson's disease; and multi-infarct dementia. The therapy is delivered by stimulation of the vagus nerve to modulate the vagal activity of the patient in a predetermined manner to treat and relieve the symptoms of the disorder, rather than the underlying root cause of the disorder.

According to the invention, either of two related therapies may be employed for treating dementia, depending upon the patient and the EEG characteristics. Both treatments involve desynchronization of the EEG, and in some patients both modalities may be used at different times. Synchronization is present when the EEG has a periodic component, whereas desynchronization is characterized by the appearance of completely random EEG activity. The choice of therapeutic modality is determined by whether slow wave or paroxysmal activity is present in the EEG. When high voltage synchronous slow wave activity predominates in the EEG, stimulus parameters designed to desynchronize the EEG and increase the rate of background activity will be chosen. When synchronous paroxysmal discharges are present, the vagus nerve will be stimulated in such a way as to desynchronize the EEG, but not affect the background rate. Both modalities may be used in patients whose EEGs do not exhibit paroxysmal activity since such activity may be present but not detectable. The two modalities may be used intermittently.

One theory advanced by the applicants herein for the effectiveness of the treatment is that because both of these abnormal EEGs exhibit synchronous waveform patterns and activities, desynchronization may cause reversion to a normal or quasi-normal EEG pattern. Assuming that a driving phenomenon in the brain stem produces slow wave activity, for example, blockage of the driver can produce the desired effect. The clinical state may also be the result of an abnormally low activity of a brain stem driver, which is activated by vagal stimulation. As noted above, such therapy only treats the symptoms of the disorder to increase the patient's functional level, and is unlikely to cause an alteration of the underlying pathophysiology of the disease, but can be extremely beneficial nevertheless.

In each case, treatment is carried out by applying specially adapted modulating electrical signals to the patient's vagus nerve. The modulating signals are generally designed to be stimulating, although inhibiting signals may be desirable in some instances. For purposes of this disclosure, the term "stimulating" is frequently used to encompass both stimulation and inhibition. It should be emphasized that although the preferred and apparently most effective nerve site for application of the modulating signals is the vagus nerve, effective treatment may be available by application to one or more other nerves, particularly among the cranial nerves, and such treatment is deemed to be within the ambit of the present invention. The invention recognizes and employs specific techniques of vagal stimulation in a therapeutic regimen for treatment of dementia of all types.

Selection among various strategies for vagal modulation to treat a particular type of dementia will depend on a number of factors. This includes such factors as (i) a consideration of which of the nerve fibers are to be subjected to the modulation; (ii) the modality for achieving desynchronization (iii) whether some type of physiologic signal is generated which can be detected and employed to trigger the modulation; and/or (iv) whether a "carryover" or refractory period occurs after modulation in which the benefit of the modulation is maintained. These are not all of the factors to be considered for selecting a stimulation strategy for treatment of a particular disorder, nor are they necessarily listed in order of importance, but are indicative of considerations which may apply in a specific case.

Proper selection of amplitude and frequency range of the applied signal is important for desynchronizing the EEG. In general, desynchronization is achievable by stimulation with signal levels in the range from about 0.1 volt to about 3.0 volts, at frequencies in the range from 20 to 75 Hz; and with signal levels greater than approximately 3.0 volts, at frequencies above 75 Hz. However, the actual voltage required depends on the type and geometry of the electrode and the impedance of the electrode-tissue interface.

The present invention also uses different signal parameters and threshold curves to activate the various fibers of a patient's vagus nerve for selective modulation thereof, in the treatment of the dementia. By appropriately setting pulse width and amplitude of the electrical signal to be delivered by the neurostimulator to the patient's vagus nerve, the nerve fibers can be selectively stimulated. Various related factors, however, must be considered in the selection process. For example, because the C fibers conduct signals very slowly, they are not highly responsive to techniques of fast stimulation. Therefore, if it were desired to desynchronize by stimulation of the C fibers at 50 Hz, for example, for treatment of a particular type of dementia, it would be prudent to use a short pulse train for the stimulus. This is because the fibers would become refractory to the stimulation within a relatively short time interval and thus incapable of tracking the pattern of a longer train. After a suitable recovery period, another short pulse train may be applied to achieve further treatment. The precise pattern to be used, e.g., the length of the time intervals on and off, will depend upon and be adjusted to the individual patient and the particular type of dementia being treated.

According to the preferred method of the invention, the stimulation strategy is to modulate the activity of a number of brain structures, including the reticular formation, hippocampus and cortex. The cortex is probably the more important structure in dementia, and, therefore, cortical activation is likely to be more important in the treatment of dementia. As described by Rutecki in *Epilepsia* (1990) 31 (Supp. 2): S1–S6, the vagus nerve projects directly or indirectly to a number of brain structures. The reticular formation system is involved with modulating the level of alertness. During drowsiness and slow wave sleep, the reticular system reduces brain level activity and the EEG is associated with high voltage, slow wave synchronous activity. Since this type of activity is frequently seen in patients with dementia, activating the reticular formation via vagal modulation may alter the patient's EEG to a more activated state and improve the clinical status. Modulation of hippocampal activity would be desirable for patients with paroxysmal discharges since the hippocampus is a primary focus of paroxysmal activity in many patients.

For patients with a paroxysmal EEG, episodes of abnormal brain activity may be sensed using detection circuitry in which surface or depth electrodes detect EEG changes. However, dementia is not likely to be episodic, and is recognized to be a steady decline in function. Although many patients have good and bad days, the nature of the disease indicates a need for continuous treatment. Preferably, therefore, the stimulation strategy is implemented by activation of the stimulus generator to continuously generate an electrical signal appropriate for application to the patient's vagus nerve to modulate the activity of the brain structures including cortex, reticular formation and hippocampus, by which to desynchronize the synchronous high voltage slow wave, and increase the background activity. Alternatively, an intermittent stimulation pattern applied at random intervals over the course of each day (i.e., during daytime hours only, and turned off at night) may be programmed into the implanted stimulus generator from the external electronics.

Accordingly, it is a principal object of the present invention to provide improvements in methods and apparatus for treating and controlling dementia.

It is a more specific object of the invention to provide methods of treating and controlling dementia by stimulation of the patient's vagus nerve to selectively modulate vagal activity.

A further object of the invention is to provide methods of and apparatus for treating and controlling dementia by applying electrical stimuli to the patient's vagus nerve to activate a group of the nerve fibers for modulating the activity of certain of the brain structures to desynchronize the patient's EEG, according to the specific nature of the dementia.

BRIEF DESCRIPTION OF THE DRAWINGS

The above and still further objects, aspects, features and attendant advantages of the present invention will be better understood from a consideration of the ensuing detailed description of a presently preferred embodiment and method thereof, taken in conjunction with the accompanying drawings, in which:

FIG. 1, described above, constitutes, in parts (a), (b), and (c), simplified representations of EEG patterns exhibiting normal activity, slow wave activity, and paroxysmal discharges;

FIG. 2, also described above, is a simplified chart plotting intellectual function versus age for the general population and for patients with Alzheimer's disease;

FIG. 3 is a simplified block diagram of an implantable neurostimulator electronics package (stimulus generator) for use (with appropriate parameter settings and ranges) in treating dementia according to the present invention;

FIG. 4 is a simplified fragmentary illustration of the stimulus generator and lead/electrode system of the neurostimulator implanted in the patient's body;

FIG. 5 is a detailed fragmentary illustration of the nerve electrode as implanted on the vagal nerve in the neck of the patient for modulating vagal activity; and FIG. 6 is an illustrative idealized electrical output signal waveform of the stimulus generator useful for clarifying relevant parameters of the signal.

DESCRIPTION OF THE PRESENTLY PREFERRED EMBODIMENT AND METHOD

Referring now to the drawings, a block diagram of the basic components of the stimulus generator of a neurostimulator and their interrelationship is illustrated in FIG. 3, and further details of location of an implantable version of the device and the associated lead/electrode system are shown in FIGS. 4 and 5. A generally suitable form of neurostimulator for use in the apparatus of the present invention is disclosed in copending U.S. patent application Ser. No. 07/434,985, filed Nov. 13, 1989, now U.S. Pat. No. 5,154,172 dated Oct. 13, 1992, (referred to herein as "the '172 patent"), assigned to the same assignee as the instant application. The specification of the '172 patent is incorporated herein in its entirety by reference, but for the sake of convenience to the reader, certain portions of it are summarized in this application.

The neurostimulator utilizes a conventional microprocessor and other standard electrical and electronic components, and in the case of an implanted device, communicates with a programmer and/or monitor located external to the patient's body by asynchronous serial communication for controlling or indicating states of the device. Passwords, handshakes and parity checks are employed for data integrity. The neurostimulator also includes means for conserving energy, which is important in any battery operated device and especially so where the device is implanted for medical treatment of a disorder, and means for providing various safety functions such as preventing accidental reset of the device.

The stimulus generator 10 (FIG. 3) is preferably adapted to be implantable in the patient's body, in a pocket formed by the surgeon just below the skin in the chest as shown in FIG. 4, although a primarily external neurostimulator may alternatively be employed. The neurostimulator also includes implantable stimulating electrodes (described below) together with a lead system 22 for applying the output signal of the stimulus generator to the patient's vagus nerve. Components external to the patient's body include a programming wand for telemetry of parameter changes to the stimulus generator and monitoring signals from the generator, and a computer and associated software for adjustment of parameters and control of communication between the generator, the programming wand and the computer. The external components of the system are not shown in the drawings.

In conjunction with its microprocessor-based logic and control circuitry, the stimulus generator 10 may include detection circuitry for sensing specific characteristics of the patient's EEG by which to trigger automatic delivery of the stimulating signal only at those times when the abnormal activity is present. However, electrodes for detecting the EEG require complex and delicate implantation procedures, and in any event continuous treatment is preferred (including such treatment which may be interrupted intermittently and/or applied only during the patient's normal waking hours), and consequently, a separate detection system is not employed in the preferred embodiment. The stimulus generator is designed, implemented and programmed to deliver a selectively patterned stimulating signal to modulate vagal activity in a manner designed to treat the specific type of dementia of interest.

As shown in FIG. 3, stimulus generator 10 includes a battery (or set of batteries) 12, which may be of any reliable long-lasting type conventionally employed for powering implantable medical electronic devices (such as batteries employed in implantable cardiac pacemakers or defibrillators). In the preferred embodiment of the stimulus generator, the battery is a single lithium thionyl chloride cell. The terminals of the cell 12 are connected to the input side of a voltage regulator 13. The regulator smoothes the battery output to produce a clean, steady output voltage, and provides enhancement thereof such as voltage multiplication or division if necessary for a specific application.

Regulator 13 supplies power to logic and control section 15, which includes a microprocessor and controls the programmable functions of the device. Among these programmable functions are output current, output signal frequency, output signal pulse width, output signal on-time, output signal off-time, daily treatment time for continuous or periodic modulation of vagal activity), and output signal-start delay time. Such programmability allows the output signal to be selectively crafted for application to the stimulating electrode set (FIGS. 4 and 5) to obtain the desired modulation of vagal activity for treatment and control of the type of dementia of interest. Timing signals for the logic and control functions of the generator are provided by a crystal oscillator 16.

Built-in antenna 17 enables communication between the implanted stimulus generator and the external electronics (including both programming and monitoring devices) to permit the device to receive programming signals for parameter changes, and to transmit telemetry information, from and to the programming wand. Once the system is programmed, it operates continuously at the programmed settings until they are reprogrammed (by the attending physician) by means of the external computer and the programming wand.

Logic and control section 15 of the stimulus generator 10 controls an output circuit or section 19 which generates the programmed signal levels appropriate to the dementia being treated. The output section and its programmed output signal are coupled (directly, capacitively, or inductively) to an electrical connector 20 on the housing 21 of the generator and to lead assembly 22 connected to the stimulating electrodes (FIGS. 4 and 5). Thus, the programmed output signal of stimulus generator 10 may be applied to the electrode set implanted on the patient's vagus nerve, to modulate vagal activity in a desired manner to treat and control the dementia and, as well, to enhance the patient's ability to control the voluntary motor functions affected by the dementia.

Housing 21 in which stimulus generator 10 is encased is hermetically sealed and composed of a material such as titanium which is biologically compatible with the fluids and tissue of the patient's body. Further details of suitable structure and operation of the neurostimulator, beyond those by which the device is adapted to treat dementia,. as described herein, are available in the '172 patent, to which the reader is referred. Although not used in the preferred embodiment, if a detection system is employed with the neurostimulator to detect characteristics of the EEG by which to initiate the vagal stimulation automatically, the signal parameters of the implanted device may be calibrated by telemetry (via the programming wand) to the particular patient and the results then programmed into the microprocessor for the appropriate treatment.

FIG. 4 illustrates the preferred location of implanted generator 10, in case 21 with connector 20, in the patient's chest in a cavity formed by the implanting surgeon just below the skin, much as a pacemaker pulse generator would be implanted. A stimulating nerve electrode set 25 (FIG. 5) is conductively connected to the distal end of insulated electrically conductive lead assembly 22 which is attached at its proximal end to connector 20. Electrode set 25 is a bipolar stimulating electrode, preferably of the type described in U.S. Pat. No. 4,573,481 issued Mar. 4, 1986 to Bullara. The electrode assembly is surgically implanted on the vagus nerve 27 in the patient's neck. The two electrodes 25-1 and 25-2 are wrapped about the vagus nerve, and the assembly is secured to the nerve by a spiral anchoring tether 28 preferably as disclosed in U.S. Pat. No. 4,979,511 issued Dec. 25, 1990 to Reese S. Terry, Jr. and assigned to the same assignee as the instant application. Lead(s) 22 is secured, while retaining the ability to flex with movement of the chest and neck, by a suture connection 30 to nearby tissue.

The open helical design of electrode assembly 25 (described in detail in the above-cited Bullara patent), which is self-sizing and flexible, minimizes mechanical trauma to the nerve and allows body fluid interchange with the nerve. The electrode assembly conforms to the shape of the nerve, providing a low stimulation threshold by allowing a larger stimulation contact area. Structurally, the electrode assembly comprises two ribbons of platinum constituting the electrodes which are individually bonded to the inside surface of each of the first two spiral loops 25-1 and 25-2 of a three-loop helical assembly, and the two lead wires are respectively welded to the conductive ribbon electrodes. The remainder of each loop is composed of silicone rubber, and the third loop acts as the tether 28 for the electrode assembly. The inner diameter of the helical bipolar electrode assembly may typically be approximately two millimeters (mm), and an individual spiral is about seven mm long (measured along the axis of the nerve).

The stimulus generator may be programmed with an IBM-compatible personal computer (not shown) using programming software of the type copyrighted by the assignee of the instant application with the Register of Copyrights, Library of Congress, or other suitable software based on the description herein, and a programming wand (not shown). The wand and software permit noninvasive communication with the generator after the latter is implanted. The wand is powered by internal batteries, and has a "power on" light to indicate sufficient power for communication. Another indicator light shows that data transmission is occurring between the wand and the generator.

The operation of stimulus generator 10 to control and treat dementia will be described with reference to FIG. 6, which illustrates the general nature, in idealized representation, of the output signal waveform delivered by output section 19 of the neurostimulator to electrode assembly 25. This illustration is presented principally for the sake of clarifying terminology, including the parameters of output signal on-time, output signal off-time, output signal frequency, output signal pulse width, and output signal current.

The preferred range of stimulation parameters of the output signal for treatment and control of dementia, and the typical value of each parameter of the output signal programmed into the device by the attending physician are set forth in the following table.

|  | Range | Desynch (Slow Wave) Typical | Desynch (Paroxysmal) Typical |
| --- | --- | --- | --- |
| Pulse Width | 0.05–1.5 ms | 0.5 ms | 0.5 ms |
| Output Current | 0.1–5.0 mA | 1.5 mA | 3.0 mA |
| Frequency | 5–150 Hz | 25 Hz | 80 Hz |
| On Time | 5–500 sec | 300 sec | 30 sec |
| Off Time | 5–500 sec | 10 sec | 300 sec |
| Frequency sweep? | 10–50 Hz | Yes (optional) | |
| Random frequency? | 10–50 Hz | Yes (optional) | |

The device may utilize circadian programming in place of a constant periodic signal pattern or a continuous (with or without intermittent interruption) signal pattern so that activation takes place automatically, but only during the normal waking hours of the patient. The treatment or therapy administered through such selective vagal stimulation serves to achieve the desired effects of modulation of the activity of a number of the brain structures to desynchronize the EEG, and thereby to suppress the confusion, disorientation, stupor and/or apathy otherwise experienced by the patient.

Various features may be incorporated into the neurostimulator for purposes of the safety and comfort of the patient. For example, comfort would be enhanced by programming the output stimulus to ramp up during the first two seconds of stimulation, rather than to be delivered abruptly. Also, the implanted generator may be provided with a clamping circuit to limit the maximum voltage, to 14 volts for example, which is delivered to the vagus nerve. Such a maximum limit is designed to prevent damage to the patient's vagus nerve.

The programmable functions and capabilities of the neurostimulator are designed and implemented to permit noninvasive communication with the stimulus generator after it is implanted, which is useful for both activation and monitoring functions. Beyond the essential functions of the device, the programming software may readily be structured to provide straightforward menu-driven operation, HELP functions, prompts, and messages to facilitate simple and rapid programming while keeping the user fully informed of everything occurring at each step of a sequence. Programming capabilities should include capability to modify the adjustable parameters of the stimulus generator and its output signal, to test device diagnostics, and to store and retrieve telemetered data. It is desirable that when the implanted unit is interrogated, the present state of the adjustable parameters is displayed on the monitor of external PC so that the programmer may then conveniently change any or all of those parameters at the same time; and, if a particular parameter is selected for change, all permissible values for that parameter are displayed so that the programmer may select an appropriate desired value for entry into the neurostimulator.

Diagnostics testing should be implemented to verify proper operation of the device, and to indicate the existence of problems such as with communication, the battery, or the lead/electrode impedance. A low battery reading, for example, would be indicative of imminent end of life of the battery and need for implantation of a new device. The nerve electrodes are capable of indefinite use absent indication of a problem with them observed on the diagnostics testing.

Although a preferred embodiment and methods of treating and controlling dementia through vagal modulation according to the invention have been described herein, it will be apparent to those skilled in the field from a consideration of the foregoing description that variations and modifications of such embodiments, methods and techniques may be made without departing from the true spirit and scope of the invention. For example, although a totally implantable device is preferred, the electronic energization package may, if desired, be primarily external to the body. Stimulation can be achieved with an RF power device implemented to provide the necessary energy level. The implanted components may be limited to the lead/electrode assembly, a coil and a DC rectifier. Pulses programmed with the desired parameters would be transmitted through the skin with an RF carrier, and the signal thereafter rectified to regenerate a pulsed signal for application as the stimulus to the vagus nerve to modulate vagal activity. This would virtually eliminate the need for battery changes. The disadvantages of such an implementation are that the external transmitter must be carried by the patient, greater power is required for activation, and the output current to the nerve is less stable.

An external stimulus generator may be employed with leads extending percutaneously to the implanted nerve electrode set. The major problem encountered with this technique is the potential for infection, but it is useful to allow short term testing of the patient to determine whether the type of dementia suffered by this particular patient is amenable to successful treatment. If it is, a more permanent implant may be provided.

Accordingly, it is intended that the invention shall be limited only to the extent required by the appended claims and the rules and principles of applicable law.

What is claimed is:

1. A method of treating patients with dementia, which comprises the steps of:
   selecting a patient suffering from dementia, and
   applying a stimulating signal with predetermined electrical parameters to the patient's vagus nerve to selectively modulate the electrical activity of preselected afferent fibers of the vagus nerve distributed to the reticular activating system in the patient's brain stem and thereby modulate the electrical activity of preselected portions of the reticular activating system of the patient, to relieve a symptom of the dementia.

2. The method of claim 1, including
   applying said stimulating signal to the patient's vagus nerve via a nerve electrode implanted on the nerve in the patient's neck.

3. The method of claim 1, including
   applying said stimulating signal continuously to the patient's vagus nerve.

4. The method of claim 1, including
   applying said stimulating signal periodically to the patient's vagus nerve.

5. The method of claim 1, including
   applying said stimulating signal intermittently to the patient's vagus nerve.

6. The method of claim 1, including
   setting electrical parameters including timing and amplitude of said stimulating signal to stimulate said preselected afferent fibers of the patient's vagus nerve.

7. The method of claim 6, including
   implanting a neurostimulating device into the patient to generate said stimulating signal for application to the patient's vagus nerve.

8. The method of claim 7, including
   formulating the stimulating signal as a predetermined sequence of electrical pulses for application to the patient's vagus nerve.

9. The method of claim 8, further including
   selectively setting parameter values of the sequence of electrical pulses including pulse width, output current, frequency, on time and off time, for the selective modulation of electrical activity of said preselected portions of the reticular activating system of the patient.

10. A method for treating and controlling symptoms of dementia in a patient, which comprises the steps of:
    selecting a patient suffering from dementia,
    implanting an electrode on the patient's vagus nerve for application of an electrical signal having predetermined electrical parameter values to the vagus nerve, and
    delivering the electrical signal to the implanted electrode to selectively modulate the electrical activity of the vagus nerve and thereby treat a symptom of the dementia exhibited by the patient.

11. The method of claim 10, including:
    setting the electrical parameter values of the electrical signal delivered to the implanted electrode for modulating the electrical activity of the vagus nerve to desynchronize the patient's electroencephalogram (EEG).

12. The method of claim 10, including:
    setting the electrical parameter values of the electrical signal delivered to the implanted electrode for modulating the electrical activity of the vagus nerve to desynchronize high voltage slow wave activity and increase background activity of the patient's EEG.

13. The method of claim 10, including:
    setting the electrical parameter values of the electrical signal delivered to the implanted electrode for modulating the electrical activity of the vagus nerve to desynchronize paraxysmal activity of the patient's EEG.

14. A method of controlling the function of a neurostimulator device adapted to be implanted in a human patient suffering from symptoms of dementia, including the steps of:
    selecting electrical parameters including pulse amplitude, pulse width and on and off times of the electrical output signal of a pulse generator of the neurostimulator device to develop an electrical signal for application to a lead/electrode assembly implanted on the vagus nerve of the patient to treat the patient's dementia by predetermined modulation of the electrical activity of the vagus nerve, and
    programming the pulse generator after implantation to set the selected parameters of its electrical output signal for treatment of the dementia when applied to the implanted lead/electrode assembly.

15. A method for use in advancing the treatment and control of symptoms of dementia in a human patient, characterized by the steps of:
    providing a lead assembly including an electrical lead having a proximal and a distal end with a stimulating electrode connected at its distal end, for implantation on the vagus nerve of a patient suffering from dementia,
    providing a programmable stimulus generator for generating electrical pulse sequences with selectively variable electrical parameters for selective application to the lead assembly when said stimulating electrode is implanted on the vagus nerve,
    incorporating an electrical connector in the stimulus generator to accommodate electrical connection of the proximal end of said electrical lead to the stimulus generators,
    restricting programmable ranges of said variables electrical parameters of the electrical pulse sequences to values which in combination will stimulate the vagus nerve and thereby modulate its electrical activity and the electrical activity of preselected portions of the reticular activating system of the patient's brain stem when one or more programmed pulse sequences are applied to the vagus nerve via the lead assembly, to vary the electrical activity of the reticular activating system in a predetermined manner according to the nature of the dementia to be treated,
    adapting the stimulus generator for restriction of the programming of the electrical parameters of the electrical pulse sequences to physician control, and
    supplying the stimulus generator and lead assembly for the treatment and control of symptoms of dementia.

16. The method of claim 15, including:
    implementing the programmable stimulus generator to include among the selectively variable electrical parameters of the electrical pulse sequences the pulse width, amplitude, frequency, sequence duration and sequence intervals.

* * * * *